(12) United States Patent
Miller et al.

(10) Patent No.: US 6,344,174 B1
(45) Date of Patent: Feb. 5, 2002

(54) GAS SENSOR

(75) Inventors: James B. Miller; Joseph D. Jolson, both of Pittsburgh, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 0 days.

(21) Appl. No.: 09/290,792

(22) Filed: Apr. 12, 1999

Related U.S. Application Data

(60) Provisional application No. 60/117,143, filed on Jan. 25, 1999.

(51) Int. Cl.[7] ............................................... G01N 27/12
(52) U.S. Cl. ............................................ 422/98; 422/90
(58) Field of Search ............................. 422/98, 90, 96, 422/51; 204/426, 429, 195; 55/486; 73/23.2

(56) References Cited

U.S. PATENT DOCUMENTS

| | | | | |
|---|---|---|---|---|
| 4,097,353 A | * | 6/1978 | Kishida et al. |
| 4,569,826 A | * | 2/1986 | Shiratori et al. |
| 5,368,713 A | * | 11/1994 | Friese et al. |
| 5,401,470 A | * | 3/1995 | Poli |
| 5,423,973 A | * | 6/1995 | Friese et al. |
| 5,494,701 A | * | 2/1996 | Clough et al. |
| 5,565,634 A | * | 10/1996 | Graessle et al. |
| 5,599,584 A | * | 2/1997 | Champney, Jr. |
| 5,841,021 A | * | 11/1998 | De Castro et al. |
| 5,902,556 A | * | 5/1999 | Van De Vyver et al. |
| 6,019,946 A | * | 2/2000 | Castillo et al. |
| 6,071,476 A | * | 6/2000 | Young |
| 6,080,219 A | * | 6/2000 | Jha et al. |

FOREIGN PATENT DOCUMENTS

| | | |
|---|---|---|
| EP | 0 094 863 | 11/1983 |
| EP | 0 130 785 | 1/1985 |
| EP | 0419282 A1 * | 9/1990 |
| EP | 0 703 449 | 3/1996 |
| GB | 2067294 A * | 7/1981 |
| GB | 2 121 180 | 12/1983 |

* cited by examiner

*Primary Examiner*—Jill Warden
*Assistant Examiner*—Brian J. Sines
(74) *Attorney, Agent, or Firm*—James G. Uber, Esq.; Henry E. Bartony, Jr., Esq.

(57) ABSTRACT

A gas sensor for the detection of gases comprises a housing and an active element disposed within the housing. The active element is surrounded by a porous insulating material having a bulk density no greater than 0.15 g/cc. Another gas sensor comprises an active element surrounded by a porous insulating material having a surface area no greater than approximately 200 m²/cc. Another gas sensor comprises a copper compound positioned so that gas contacts the copper compound before contacting the active element. Another gas sensor comprises an active element surrounded by a porous material having an average pore size of at least approximately 100 Å. Another gas sensor comprises a heating element surrounded by a porous material that supports a catalyst.

22 Claims, 8 Drawing Sheets

GAS SENSOR

This application claims benefit to U.S. provisional application Ser. No. 60/117,143, filed Jan. 25, 1999.

FIELD OF THE INVENTION

The present invention relates to a sensor for the detection of gases, and, in particular, to a sensor for the detection of gases wherein an active element is surrounded by a material of specific physical characteristics.

BACKGROUND OF THE INVENTION

A number of gas sensors or detectors include active elements at which an analyte gas is reacted for detection thereof. Combustible (flammable) gas sensors, for example, have been in use for many years to, among other things, prevent explosive accidents. Gas detectors generally operate by catalytic oxidation of combustible gases. Conventional combustible gas sensors typically include an active element comprising, for example, a platinum wire coil encased in a refractory (for example, alumina) bead, the surface area of which is covered with a catalyst. An active element comprising an encased platinum coil is commonly referred to as a pelement or a pellister. A detailed discussion of pelement and catalytic combustible gas detectors comprising such a pelement is found in Mosely, P. T. and Tofield, B. C., ed., *Solid State Gas Sensors,* Adams Hilger Press, Bristol, England (1987).

In general, the active element or pelement operates as a miniature calorimeter used to measure the energy liberated upon oxidation of a combustible gas. The platinum wire or coil serves two purposes within the pelement: (1) heating the bead electrically to its operating temperature (typically approximately 500° C.) and (2) detecting changes in temperature produced by oxidation of the combustible gas. During operation, the active element is heated to its operating temperature, where it typically catalyzes the oxidation of the combustible gas analyte(s). The heat released by the combustion reactions is detected by the active element as a temperature rise, providing a measure of the amount of combustible gas analyte present in the environment being monitored.

The increase in temperature is typically measured in terms of the variation in resistance of the platinum coil (with temperature variation). In most cases, the catalytically active element is paired with a second, inactive element or compensating element (that is, a reference resistance) for compensation of environmental factors other than combustible gas concentration, such as ambient temperature, humidity, etc. This type of sensor has been described, for example, in U.S. Pat. No. 3,092,799. The change in resistance of the active element is thus measured in relation to the change is resistance of the reference resistance. Preferably, therefore, the reference resistor comprises a compensating, nonactive element matched as closely as possible with the catalytically active element. The two resistances are part of, for example, a Wheatstone bridge circuit. The voltage developed across the circuit when a combustible gas analyte is present provides a measure of the concentration of the combustible gas.

A catalytically active element of a gas sensor can take forms other than a pelement as describe above. For example, sensors based on solid-state semi-conductor technologies have recently been developed for detection of gases. In such gas sensors, the progression of primary oxidation/reduction reaction steps as molecules of analyte gases interact with the semiconductor's surface causes its conductivity to change. The change in conductivity can be related to the concentration of analyte gases present in the atmosphere being monitored. Like the catalytic sensor, the active element of the semiconductor-based sensor is typically heated to relatively high operating temperature (for example, approximately 500° C.).

In portable, battery-powered instruments, minimization of the power consumption of gas sensors is very important to extending battery life. The industry is thus moving toward low-power gas sensors, preferably with operating voltages that match battery voltage. Most often, power reductions are achieved by employing higher resistance heaters, which are generally smaller and more fragile than their low-resistance counterparts. Catalytic beads based on coils of small diameter wire (for high resistance) are especially susceptible to breakage when a portable instrument is dropped or jarred during "normal" use. Approaches to improving the stability of low-power beads against mechanical shock include incorporation of an "insulating" layer of glass or ceramic wool to protect the elements. See U.S. Pat. No. 5,601,693. Such an insulating layer, however, can result in an increase in the power requirements of the device.

The industry has also been moving toward sensors that are more tolerant to both temporary inhibitors (such as hydrogen sulfide) and permanent poisons (such as silicones). Silicones are a particularly noteworthy class of poisons because of their debilitating effects on conventional combustible gas sensors and their increasing use in environments where combustible gas concentrations are monitored. Efforts to mitigate the effects of silicone-poisoning at the sensor level have centered on the addition of adsorbent (silicone-scavenging) materials to the bead (see U.S. Pat. Nos. 4,111,658 and 4,246,228) and coating the bead with inert layers of porous (silicone blocking) material (see U.S. Pat. No. 4,246,228).

European Patent Application No EP0094863 discloses filling the space around the active element, which is large compared to the volume of the element itself, with a zeolite adsorbent. The zeolite powder, preferably sodium Y zeolite, purportedly protects the catalytic bead from poisoning by silicone compounds without causing a discernible loss in sensitivity. It is also purported that the thermal insulating properties of the zeolite of European Patent Application No EP0094863 are conservative of sensor heat.

Although many improvements have been made in sensors for detecting gases, it remains desirable to develop sensors with improved durability, lower power requirements and/or increased poison resistance.

SUMMARY OF THE INVENTION

Generally, the present invention provides a gas sensor for the detection of gases comprising an exterior housing and an active element disposed within a housing. The active element is surrounded by a porous insulating material. Preferably, the porous insulating material has a bulk density of less than 0.3 g/cc. More preferably, the porous insulating material has a bulk density of less than 0.15 g/cc. Most preferably, the porous insulating material has a bulk density of less than 0.1 g/cc. It has been discovered that such low-density, porous materials increase the shock resistance of the sensor while surprisingly and effectively reducing heat losses from the active element.

As used herein in connection with the porous insulating material, the terms "surround" or "surrounding" indicate that the element is encased in or encompassed by the porous material such that the gaseous atmosphere to be tested must pass through the porous insulating material to reach the element. The surrounding porous insulating material can be in substantially any form including, for example, in powder form, in flake form, in a blanket form, or formed in place as a monolith. The porous insulating material may also be painted on the active or compensating element. Preferably, the porous insulating material is in powder form.

It has also been discovered that response time or rise time of certain analytes is inversely proportional to the surface area of porous materials surrounding an active element, particularly in the case of a porous materials comprising silica or alumina. It is believed that certain hydrocarbons, (for example, heptane and toluene) may have a weak attraction for the surfaces of materials such as silica and alumina, which can retard diffusion of such hydrocarbons to the active element and, thereby, slow response time of the detection device.

The present invention thus also provides a gas sensor for the detection of combustible gases comprising, a housing and an active element disposed within the housing. The active element is surrounded by a porous material having a surface area less than approximately 200 $m^2/cc$. More preferably, the surface are of the porous material is no greater than 100 $m^2/cc$. Even more preferably, the surface are of the porous material is no greater than 50 $m^2/cc$. Even more preferably, the surface area of the porous material is no greater than approximately 30 $m^2/cc$. Most preferably, the surface area of the porous material is no greater than approximately 20 $m^2/cc$.

The present inventors have further discovered that relatively large average pore size assists in achieving a relatively fast response or rise time, especially for larger hydrocarbons such as heptane and toluene. In that regard, the present invention also provides a gas sensor in which the active element is surrounded by a porous material preferably having an average pore size of at least approximately 100 Å. More preferably, the average pore size is at least approximately 150 Å.

With respect to the tolerance/resistance of the gas sensors to poisoning, and particularly to poisoning by silicone compounds, it has been discovered that the chemical and physical nature of the surface of materials plays a significant role. In general, poison tolerance depends upon the interaction between the poison and the solid surface. For example, the poison may retain its chemical identity while being loosely or moderately bound ("physisorbed" or "chemisorbed") to the solid surface. A poison may also chemically react at a "site" on the surface (that is, a specific arrangement of atoms on the solid). "Active" surfaces possess chemical groups that interact (via, chemisorption or reaction sites) with poisons.

Silica, for example, has a surface that is substantially inert or inactive with respect to, for example, silicon poisons. An alumina surface is an example of an active surface. Alumina, for example, has been found to be more effective in "trapping" silicone compounds such as hexamethyl disiloxane (HMDS, a model silicone compound) than a silica surface. It is believed that an alumina surface has weak acid sites, week base sites, weakly oxidizing sites and weakly reducing sites that weakly bind with such compounds. Such sites are not believed to be present on silica surfaces. Zeolites have, for example, much stronger acid sites than alumina and can be considered "more active" than alumina.

It has also been discovered that the pore volume of porous materials also has an effect upon the tolerance of the sensor to silicone poisons. In that regard, relatively large pore volumes are preferred. Preferably, the pore volume of a porous material is at least approximately 0.05 cc/cc. More preferably, the pore volume of the porous material is at least approximately 0.10 cc/cc. Surface areas, average pore sizes and pore volumes set forth in the studies of the present invention were determined by nitrogen adsorption/desorption techniques as known in the art.

In addition to the parameters discussed above as affecting tolerance/resistance of the gas sensors to poisoning, chemical compounds can be used to "scavenge" poisons from a gas sample before the gas sample reaches the active element of a gas sensor. For example, silver-containing compounds can be used as a dopant upon the surface of a porous material to transform inactive sites to active sites. Silver-containing compounds, however, can act as a catalytic material for the reaction/combustion of certain analyte gases. This catalytic activity of silver-containing compounds can result in inaccuracies, particularly when the silver-containing compounds are in the vicinity of or surrounding a compensating element.

The present inventors have discovered that copper-containing compounds improve the tolerance/resistance of gas sensors to a number of poisons, including, for example, sulfur containing compound. As copper-containing compounds are generally not catalytically active compounds for numerous analyte gases, copper-containing compounds do not suffer from the problems associated with silver-containing compounds discussed above. The present invention thus also provides a gas sensor for the detection of gases comprising an exterior housing and an active element disposed within a housing. The gas sensor further provides a copper-containing compound positioned such that a gas sample contacts the copper-containing compound before contacting the active element. As clear to one skilled in the art, the copper containing compound may be positioned either within the exterior housing of the gas sensor or outside the exterior housing. The copper compound is preferably supported upon a porous material as described above. The copper compound is preferably copper sulfate.

In another embodiment, the present invention provides a gas sensor for the detection of an analyte gas comprising, a housing and a heating element disposed within a first chamber in the housing. The heating element is surrounded by a porous material (for example, a porous powder as described above) that supports a catalyst that is suitable to catalyze a reaction of the analyte gas upon heating. In this embodiment, the heating element need not be a catalytically active element.

The gas sensors of the present invention preferably further comprises a compensating element disposed within the housing. The compensating element is preferably closely matched to the active element. In that regard, any material surrounding or in the vicinity of the active element is also preferably surrounding or in the vicinity of the compensating element.

The gas sensors of the present invention thus provides one or more of the following advantages: (1) reduced heat losses/power consumption, (2) improved tolerance to silicone-based and other poisons for longer sensor life and a more stable signal over time, (3) improved mechanical shock resistance of the sensor, and (4) reduced flow-rate dependence of sensor output.

DETAILED DESCRIPTION OF THE INVENTION

In one embodiment, the present invention describes the use of porous solid insulating materials that preferably have low thermal conductivity and low density to surround a heated active element in a gas sensor (for example, combustible gas sensors). In general, it is believed that such insulating materials can conserve or reduce energy loss from the active element by reducing heat loss via convection and radiation as compared to active element surrounded by air. The bulk thermal conductivity of the porous material should be low enough such that energy losses via thermal conduction do not offset reductions in convective energy losses and radiative energy losses.

The porous solid insulating materials preferably also have low surface area. Moreover, the porous insulating materials are preferably inert to the combustible gases to be detected and to air.

Preferably, the insulating material of the present invention comprise an oxide of a metal or a metalloid (for example, silica, alumina or zirconia) or a combination of such oxides.

In one embodiment, the insulating materials of the present invention are prepared via sol-gel chemistry to produce an aerogel. The preparation of aerogels is discussed in Ko, E., "Aerogels as Catalysts and Catalyst Supports," *Chemtech* (April 1993), the disclosure of which is incorporated herein by reference. Preferably the gel is dried under supercritical conditions (either supercritical with respect to the reaction solvent or supercritical with respect to a displacing solvent).

The insulating material(s) of the present invention may be used in any configuration of combustible gas sensors, including, but not limited to those that employ suspension of the element(s) on conducting posts and those that employ "surface mounting" of the element(s) to a track-carrying substrate. The insulating material preferably encases or surrounds at least the active element. Preferably the compensating element (if present) is also surrounded with the insulating material.

Preferably, the insulating material of the present invention is used as a powder, but the insulating material may also be in flake form, (as a blanket), or may even be formed in place as a monolith. The insulating material may be treated with dopants to enhance other aspects of sensor performance. For example, the insulating material may be doped with silver- and/or copper-containing compounds to act as scavengers for poisoning compounds. Preferably, copper-containing compounds are used.

Figure 1A:
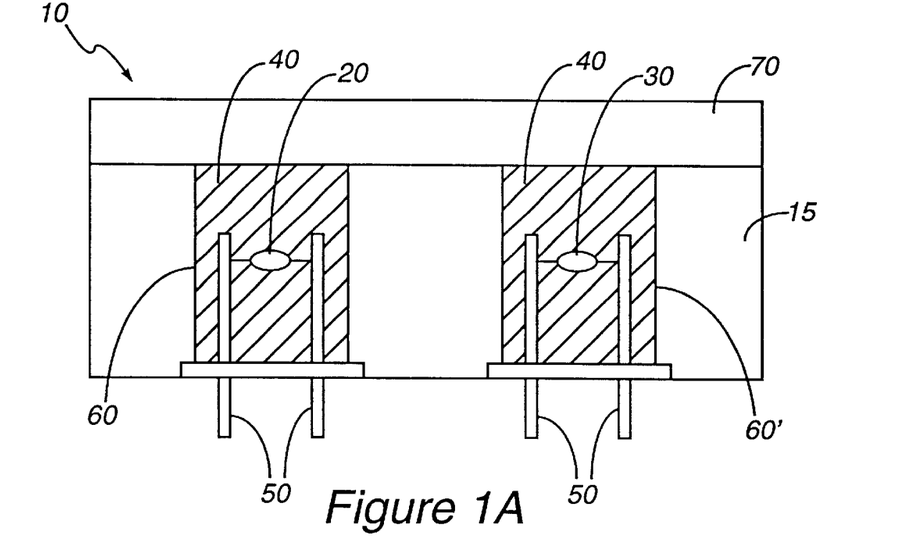
FIG. 1A illustrates a cross-sectional view of one embodiment of a combustible gas sensor of the present invention.
Figure 1B:
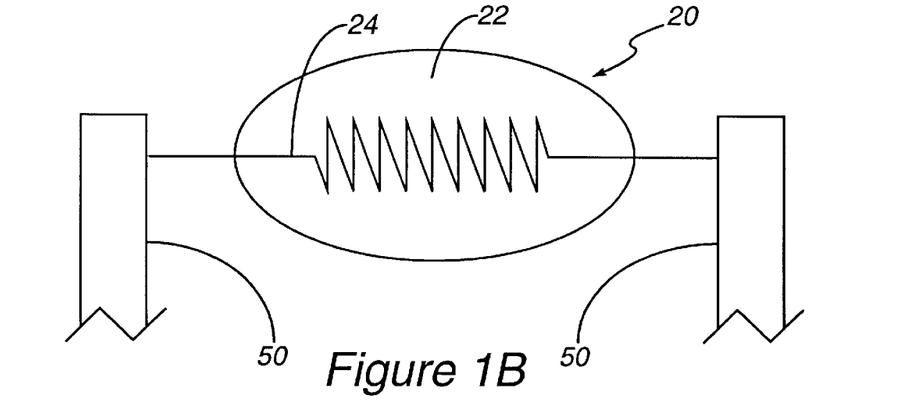
FIG. 1B illustrates a cross-sectional, exploded view of the active element of the combustible gas sensor of FIG. 1A.

Referring to FIGS. 1A and 1B, one embodiment of the present invention is illustrated. Active element 20 of sensor 10 preferably comprises a catalytic bead 22 encasing a platinum wire 24, as best illustrated in FIG. 1B. Catalytic bead 22 may comprise, for example, a ceramic substrate with a palladium or platinum catalyst as known in the art. Active element 20, and preferably also compensating element 30 (if present), are surrounded by a volume of a porous insulating material 40 that is preferably large compared to the volume of each of active element 20 and compensating element 30. When active element 20 and compensating element 30 are mounted on conducting posts 50, insulating material 40 is preferably in powder or flake form, and it is preferably enclosed by cylindrical wells or chambers 60 and 60' bored or molded into a housing 15 (for example, a plastic or metal housing) as shown in FIG. 1. In a typical case, the volume of active element 20 is preferably less than 0.1 mm$^3$, while the volume of insulating material 40 surrounding active element 20 it is preferably greater than 100 mm$^3$. Combustible gas sensor 10 also preferably includes a flashback arrestor 70 such as a porous frit as known in the art.

In the case of elements mounted on a "track carrying substrate," the insulating material is preferably and more conveniently applied in the form of a blanket or monolith. In both mounting arrangements, the insulating material cushions the active and compensating elements against physical shock, thermally insulates the active and compensating elements, and protects the active and compensating elements from various environmental poisons (most notably silicones).

EXAMPLES

Example 1

A catalytic combustible gas sensor as described in FIGS. 1A and 1B with empty wells was used to sense a mixture of 2.5% vol of methane in air. The output of the active element was measured as a function of power input supplied to the active element. The resulting operating curve for the active element surrounded by air is labeled A in FIG. 2A. The experiment was repeated with the well of the active element filled with several powders, using a different powder in each experiment. The resulting operating curves for, SIP22ls precipitated silica available from Degussa Corp. (bulk density of approximately 0.067 g/cc), an aerogel available from Aspen Systems (bulk density of approximately 0.056 g/cc), an alumina available from Atomergic (bulk density of approximately 0.19 g/cc), UOP LZY64 zeolite available from UOP (bulk density of approximately 0.34 g/cc) and 645 silica gel available from Davison are labeled B through F, respectively, in FIG. 2A. Each sample was "heat treated" for approximately two hours in still air at a temperature in the range of approximately 500 to approximately 860° C.

Figure 2A:
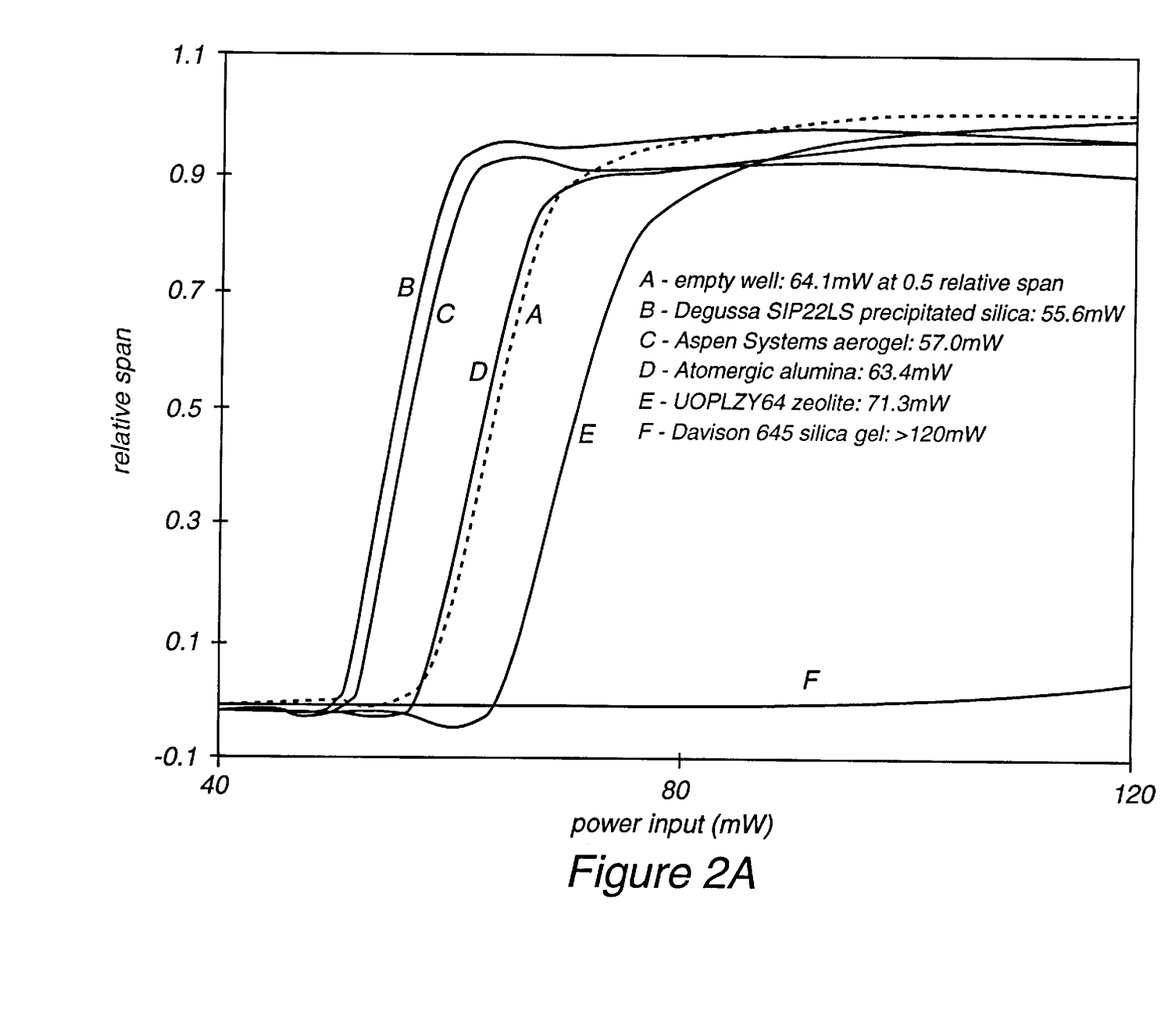
FIG. 2A illustrates a study of the output of a combustible gas sensor of the present invention in which the active element thereof is surrounded by air and by various insulating materials.

Compared with an empty well (no insulator, curve A), Degussa SIP22LS precipitated silica (curve B), Aspen Systems silica aerogel (curve C), and Atomergic alumina (curve D) surprisingly lowered the power input required for the active element to reach the temperature for methane combustion (that is, the operating curve shifts to lower power). When the well was filled with UOP LZY64 zeolite (curve E; the zeolite described in European Patent Application No. EP0094863), the power input increased approximately 10% from the empty well case. A conventional dense silica gel, Davison 645 silica gel (curve F) increased active element power consumption substantially.

Like other insulating materials, the materials of the present invention improve the mechanical shock resistance of fragile, high-resistance elements. However, the ability of such materials to conserve or even lower power consumption with relatively small reduction in the output signal is a very unexpected result and represents a significant improvement to the current state of the art of combustible gas sensors.

Figure 2B:
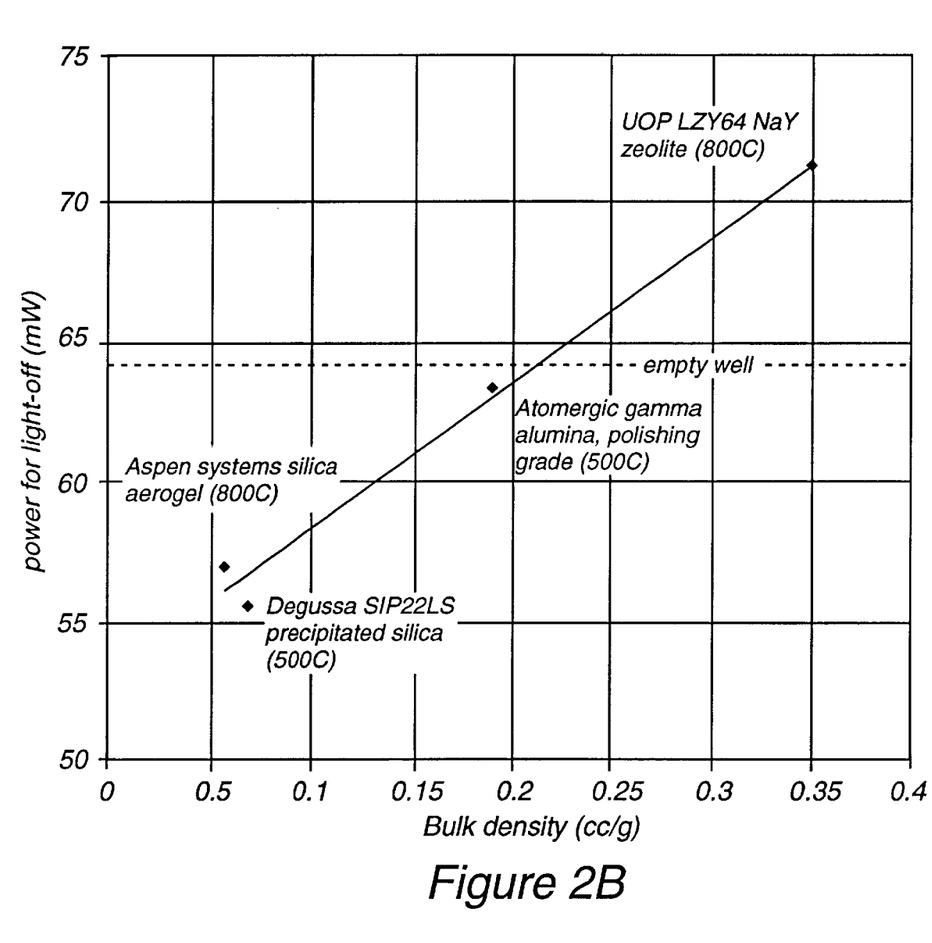
FIG. 2B illustrates the effect of bulk density upon power consumption.

The reduction in power consumption experienced with the insulating materials of the present invention is believed to be a result of the relatively low density of the insulating materials of the present invention as compared to prior insulating materials. In that regard, a study of the effect of powder bulk density upon power consumption of a combustible gas sensor of the present invention is set forth in FIG. 2B.

Example 2

A catalytic combustible gas sensor with empty wells (that is, with no insulating material surrounding the elements) was used to sense a mixture of 2.5% vol of methane in air containing 15 ppm of a hexamethyldisiloxane (HMDS) silicone poison. Output of the active element at constant input power was monitored over time. The time that elapsed when the active element's output declined to one half of its initial value was recorded as the "half-life in 15 ppm HMDS." The experiment was repeated with the well of the active element filled with silica aerogel powder. The experiment was repeated also for each of two commercially available sensors designed specifically for silicone tolerance. The results appear in Table 1.

TABLE 1

| insulator/sample | half-life in 15 ppm HMDS |
|---|---|
| none (empty well) | 25 minutes |
| silica aerogel | 4.5 hours |
| commercially available sensor #1 | 7 minutes |
| commercially available sensor #2 | 1 hour |

Commercially available sensor #1 was a CiTipel 4P-50 combustible gas sensor available from City Technology Limited of Portsmouth, England. Commercially available sensor #2 was an EEV VQ542ZD combustible gas sensor available from EEV of Essex, England.

As set forth in Table 1, silica aerogel was found to extend the life of the active element in a silicone-containing atmosphere by more than a factor of 10 as compared to an active element with no insulating material. The aerogel insulating material was also found to be superior to the commercially available silicone-tolerant sensors tested.

Example 3

A catalytic combustible gas active element as illustrated in FIGS. 1A and 1B was placed in an aerogel-filled well and was powered in ambient air with no added silicones. On days 0, 7 and 49, operating curves for 2.5% vol of methane in air were obtained as described in Example 1. A second active element was placed in an empty well and was subjected to the same experimental protocol. For both active elements, maximum sensor span and power input required to reach 50% of maximum span were recorded as a function of time.

Figure 3:
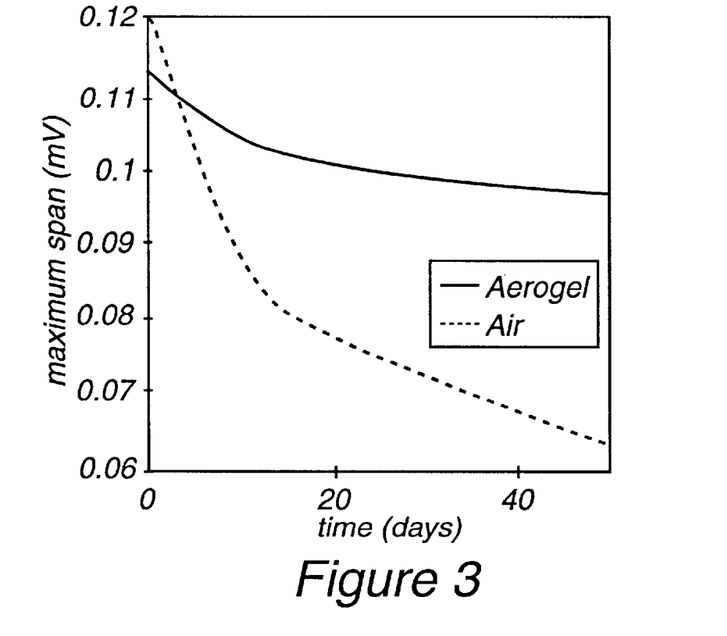
FIG. 3 illustrates graphically a comparison of the stability of an active element surrounded by air and the stability of an active element surrounded by an aerogel.
Figure 4:
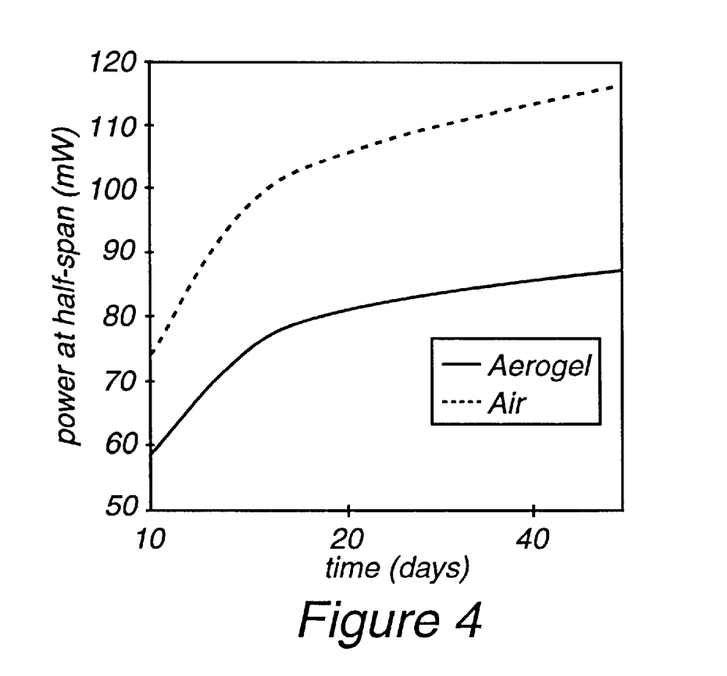
FIG. 4 illustrates a comparison of the power input required for methane combustion to commence for an active element surrounded by air and for an active element surrounded by an aerogel.

FIG. 3 illustrates that sensor span was more stable when the detector or active element was surrounded with an aerogel. FIG. 4 illustrates that the power input required for methane combustion to commence (location of the operating curve) was also more stable when the active element was surrounded with an aerogel. These results illustrate the ability of the porous insulating material of the present invention to protect the active element from low-level poisons present in ambient air, thereby increasing the life of the element.

Example 4

None of the insulating materials of the present experiments significantly affected response times for methane. There were, however, important effects on response times for higher hydrocarbons. In one experiment, a catalytic combustible active element located in an empty well was used to sense 0.7% vol of n-heptane in air. Output of the active element at constant input power was monitored over time. The period of time that elapsed between the time the sensor was first exposed to heptane and the time the active element's output rose to half of its final value was recorded as "$T_{50}$ for n-heptane." The experiment was repeated with the well of the active element filled with several porous powders. The results of these studies appear in Table 2.

TABLE 2

| Insulator | Surface Area ($m^2$/cc) | $T_{50}$ for n-heptane |
|---|---|---|
| None (empty well) | n.a. | 30 sec |
| Degussa SIP22LS silica | 14.5 | 2.0 min |
| Atomergic alumina | 20.3 | 2.2 min |
| Aspen silica aerogel | 36.1 | 8.0 min |
| Degussa FK500LS silica | 47.7 | 9.5 min |
| UOPLZY64 zeolite | 200 | >35 min |

The results of Table 2 show that low surface areas are desirable for quick heptane response times. As further illustrated in Table 2, the UOP LZY64 zeolite effectively prevented heptane from being detected by the active element. The insensitivity of the active element surrounded with that zeolite is believed to be primarily a result of the relatively small average pore diameter of that zeolite.

Example 5

Figure 5:
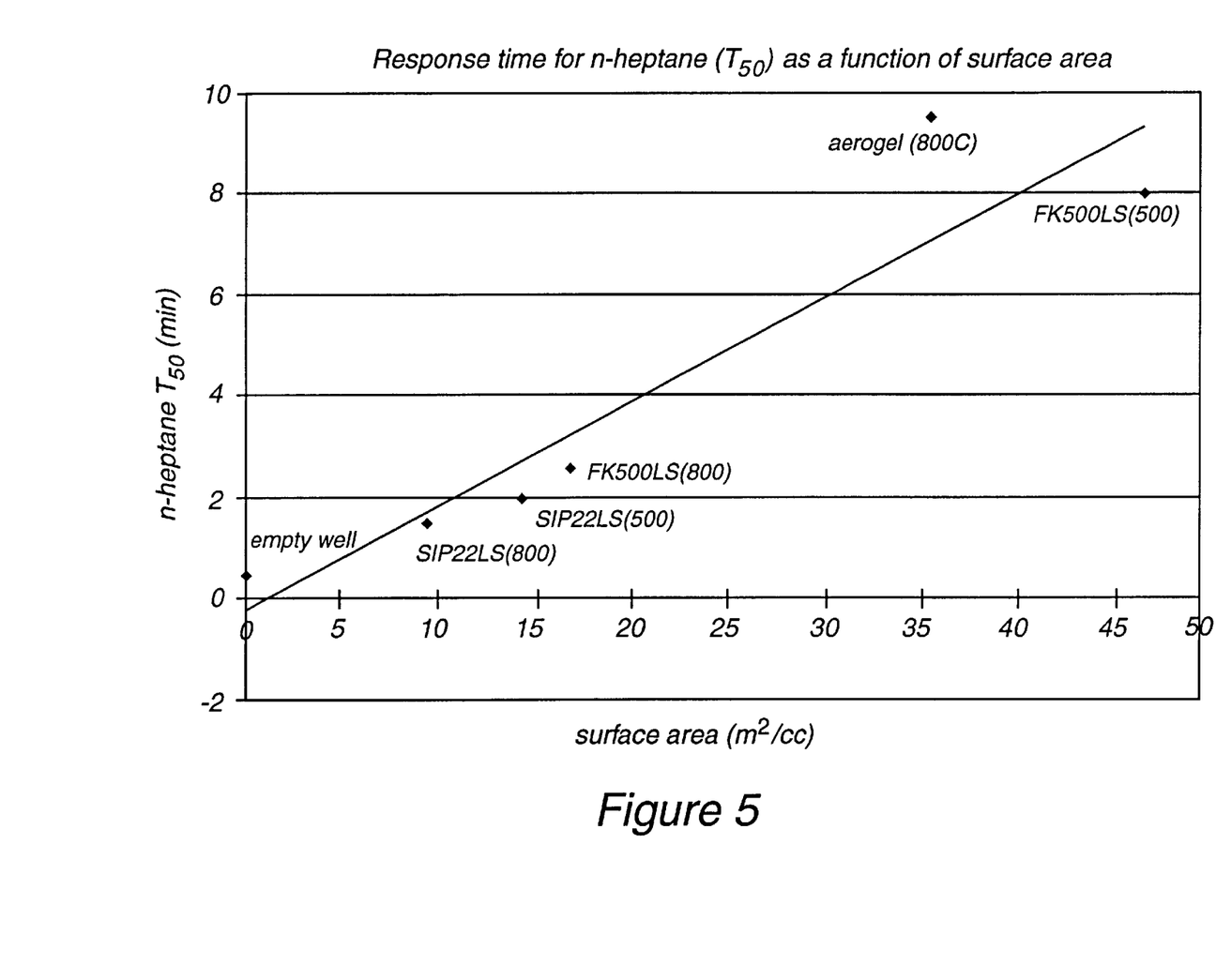
FIG. 5 illustrates a study of response time for n-heptane as a function of surface area.

To further study the effects of surface area upon response time, catalytic combustible gas sensor active elements were placed in wells filled with a number of different silica insulating materials. The chemical composition of the insulators was kept constant. An empty well was included for comparison. Each active element was exposed to 50% LEL n-heptane (0.75%) and the time required to reach 50% of maximum span ($T_{50}$) was recorded. The dependence of $T_{50}$ upon surface area of the powder is shown in the FIG. 5. This example illustrates that that low surface areas are preferred for fast response times.

SIP22LS and FK500LS are precipitated silicas made by Degussa. Heat treatment temperature are provided in parentheses in FIG. 5. Several physical characteristics of the Degussa SIP22LS and FK500LS precipitated silicas are summarized in Table 3.

TABLE 3

|  | bulk density (g/cc) | max pore diameter (Å) | pore volume (cc/g) | pore volume (cc/cc) | surface area (m2/g) | surface area (m2/cc) | average pore diameter (Å) | $T_{50}$ n-C7 (min) |
| --- | --- | --- | --- | --- | --- | --- | --- | --- |
| SIP22LS (800) | 0.081 | 250 | 0.335 | 0.027 | 115.78 | 9.39 | 115.83 | 1.5 |
| SIP22LS (500) | 0.068 | 430 | 0.672 | 0.045 | 215.16 | 14.52 | 124.87 | 2 |
| FK500LS (800) | 0.111 | 260 | 0.520 | 0.058 | 153.42 | 17.03 | 135.69 | 2.6 |
| FK500LS (500) | 0.104 | 170 | 1.259 | 0.131 | 454.17 | 47.23 | 110.86 | 8 |
| Aspen pilot aerogel | 0.056 | 190 | 1.280 | 0.071 | 649.75 | 36.13 | 78.82 | 9.5 |
| empty well |  |  |  |  | 0 | 0 |  | 0.5 |

Example 6

In another experiment, a SIP22LS silica was doped with a silver nitrate solution using an incipient wetness technique as known in the art. Without doping with silver nitrate, the half-life of a detector element surrounded by SIP22LS silica is approximately 4 minutes when exposed to 1600 ppm $H_2S$ in a background of 50% LEL methane. When the SIP22LS silica powder was doped with silver nitrate, the half-life in $H_2S$ increased to over 90 minutes. This experiment demonstrates the suitability of the porous insulating materials of the present invention to be doped with "scavenging" compounds such as a silver compound and/or a copper compound to remove undesirable poisons from the analyte gas.

Example 7

Figure 6:
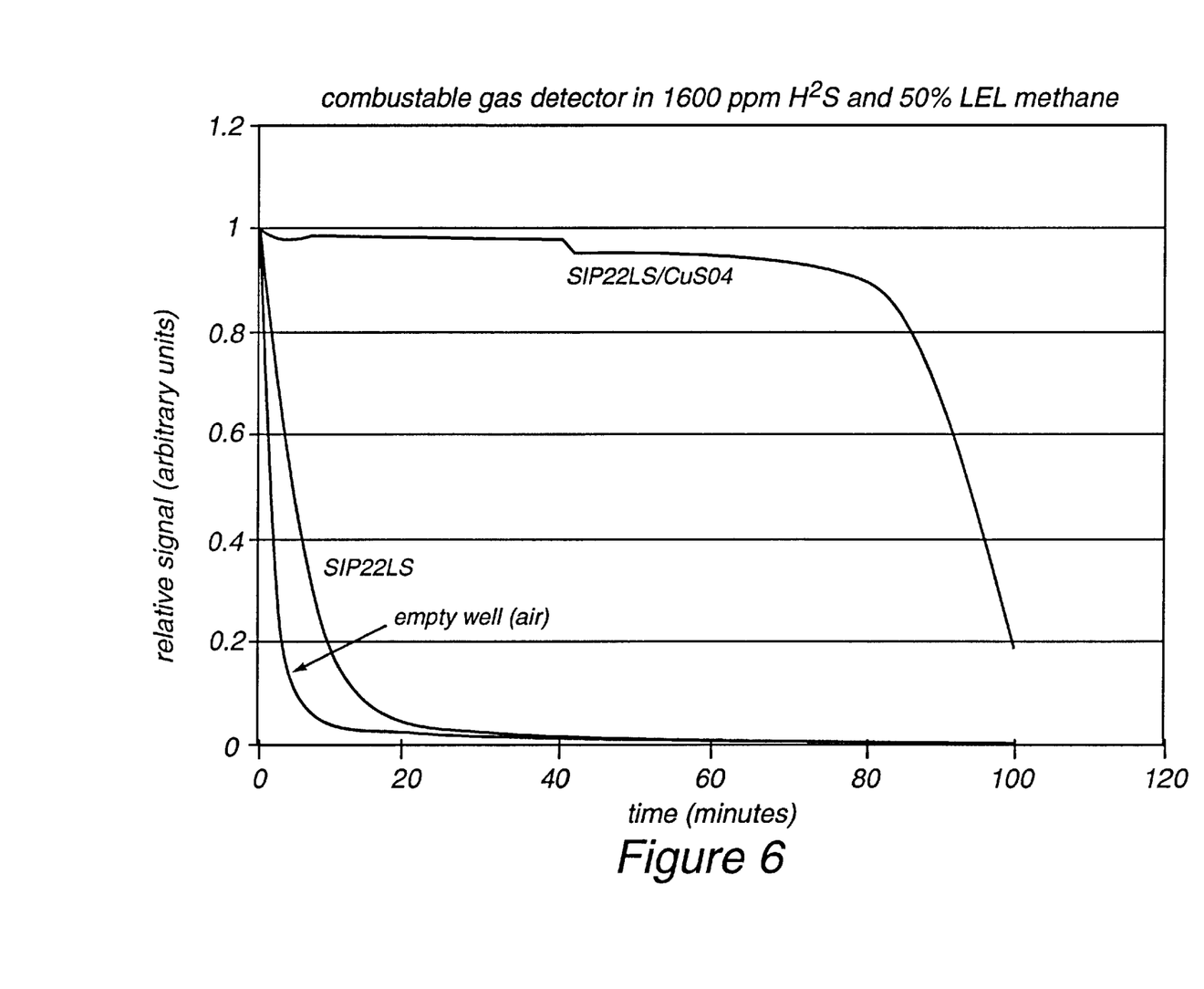
FIG. 6 illustrates a study of the effect of a copper compound dopant upon the deactivation of a sensor active element in the presence of hydrogen sulfide.

Catalytic combustible gas sensor active elements were placed in wells filled with SIP22LS silica and SIP22LS silica doped with a copper compound ($CuSO_4$); an empty well was included for comparison. At normal operating power, the elements were exposed to 1600 ppm $H_2S$ (hydrogen sulfide, a representative sulfur compound) in a background of 50% LEL methane. FIG. 6 illustrates how the output signal of each varies with time. The element in the empty well deactivates rapidly, dropping to ~20% of its initial span in under 5 minutes. The element immersed in SIP22LS deactivates somewhat more slowly, falling to 20% of its initial span in about 10 minutes. The SIP22LS doped with $CuSO_4$ retains 90% of its initial span for over an hour; 20% of initial span is reached in approximately 100 minutes.

The "undoped" SIP22LS was calcined at 850 C. SIP22LS/CuSO4 is the same silica (heat treated to 850) and doped with a saturated $CuSO_4$ solution (0.8 mL solution/1.0 g silica) and then dried at 400° C.)

Example 8

In all of the experimental examples described above, the active element comprised a pelement or pellister as illustrated in FIGS. 1A and 1B. The present inventors have discovered that the active element of the gas detection devices of the present invention can also comprise a bare wire (for example, a platinum wire without a catalyst-supporting bead thereon). Although gas detection devices comprising bare platinum wires as active elements have been used in the past, mechanical durability concerns have required that the platinum wire be relatively thick in diameter. Thin diameter wires are typically too fragile, especially for use in portable devices. The use of relatively thick wires, however, substantially increases the power required to bring the wire to a desired operating temperature.

Figure 1C:
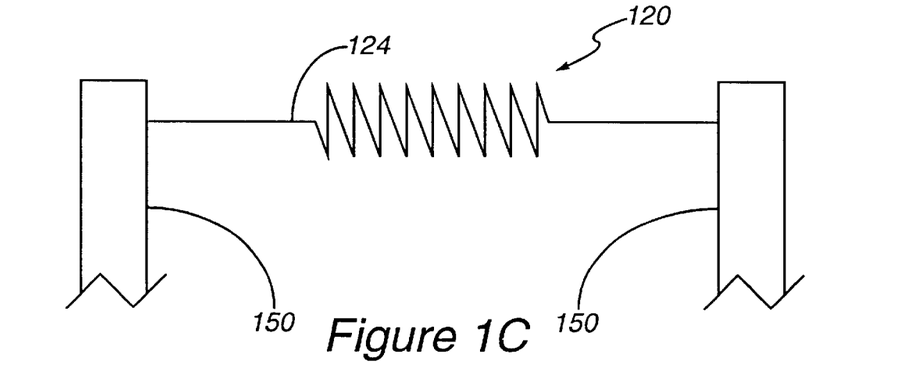
FIG. 1C illustrates a cross-sectional, exploded view of an active element consisting essentially of a platinum wire.
Figure 7:
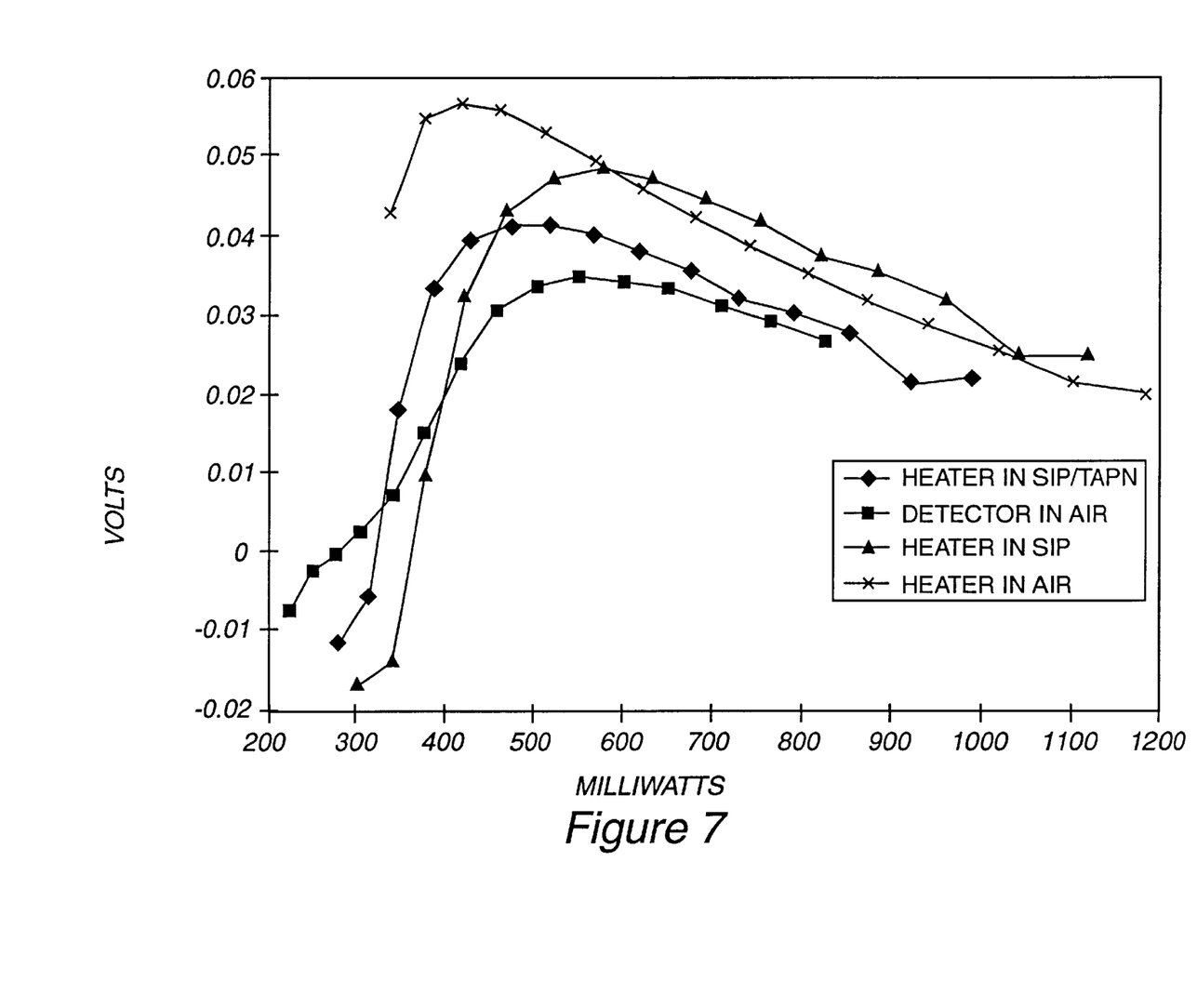
FIG. 7 illustrates a study of power consumption required for methane combustion for the active element of FIG. 1B surrounded by air, the active element of FIG. 1C surrounded by air, and for the active element of FIG. 1C surrounded by several porous insulating materials.

The present inventors have discovered that the porous insulating materials of the present invention are suitable to mechanically stabilize active elements consisting essentially of relatively thin wires (for example, platinum wires). Moreover, the thermally conservative nature of such porous insulating materials assist in maintaining power requirements for such active elements relatively low. FIG. 7 illustrates a study in which a catalytic combustible gas sensor as described in FIGS. 1A and 1B with empty wells was used to sense a mixture of 2.5% vol of methane in air. The output of the active element of FIGS. 1A and 1B was measured as a function of power input supplied to the active element. The resulting operating curve for that active element surrounded by air is labeled Detector in Air in FIG. 7. The experiment was repeated with a catalytic combustible gas sensor as described in FIG. 1C (that is, with an active element 120 consisting essentially of a platinum wire 124 supported on conducting posts 150) with empty wells. The experiment was repeated with the well of the active element of FIG. 1C (designated "Heater" in FIG. 7) filled with SIP22LS silica, and then with SIP22LS silica doped with tetraamine palladium nitrate (TAPN).

The results of FIG. 7 indicate that power requirements for a sensor comprising a bare platinum wire surrounded by a porous insulating material of the present invention closely approximate the power requirements for a conventional pelement surrounded by air. Use of a bare platinum wire surrounded by a porous insulating material of the present invention as an active element can enable substantial savings in fabrication cost with relatively little loss of mechanical stability and relatively little change in power consumption.

Example 9

Figure 8:
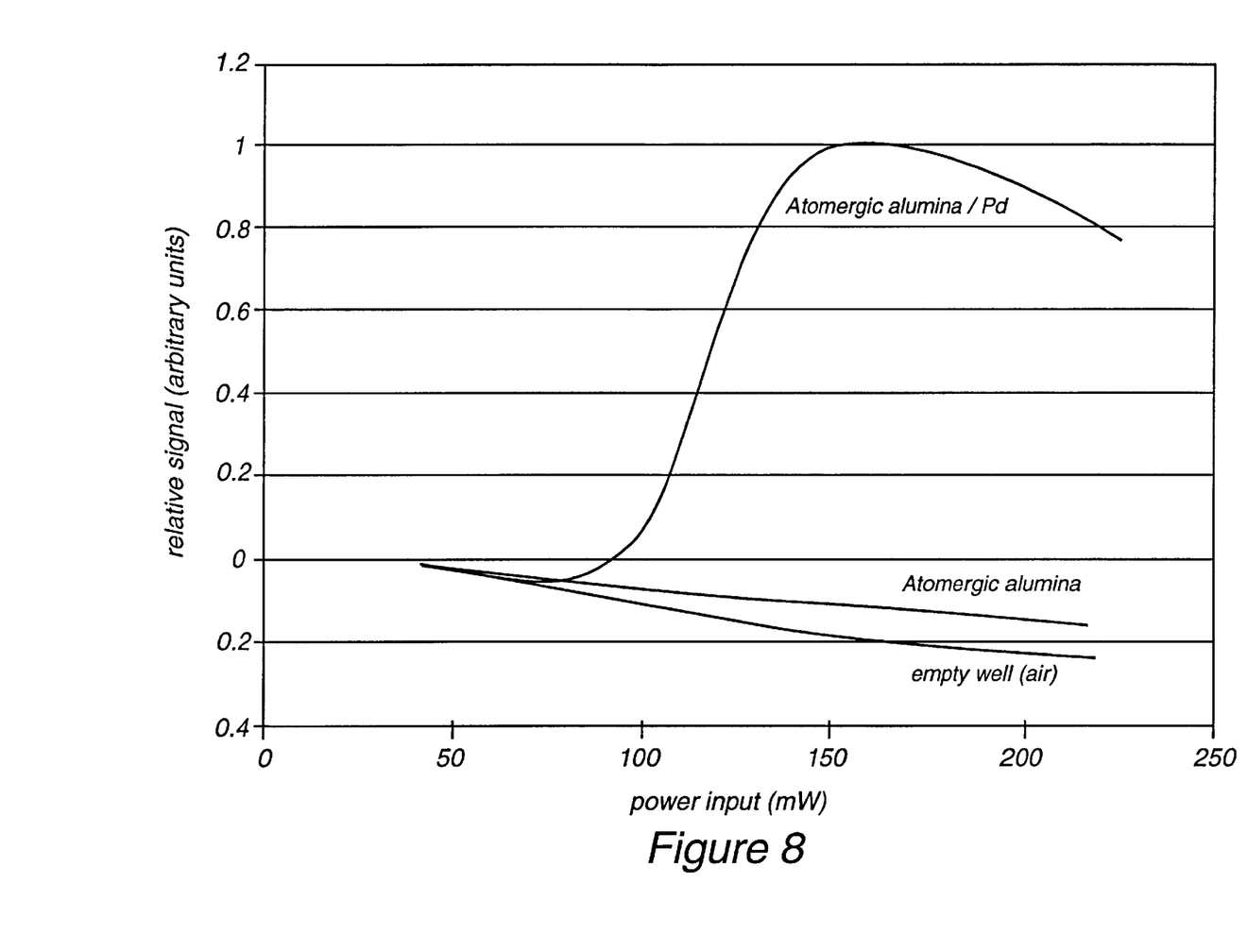
FIG. 8 illustrates a study showing that catalytic activity can be built into a substantially inactive porous insulating material of the present invention by doping with a catalyst material.

Catalytic combustible gas sensor compensator elements (inactive) were placed in wells filled Atomergic alumina and Atomergic alumina doped with tetraamine palladium nitrate (TAPN); an empty well was included for comparison. The compensator elements were exposed to 50% LEL methane and signals were recorded as a function of power input. The results are shown in FIG. 8. Neither the compensator element in the empty well nor the one in the Atomergic alumina burned methane (the negatively sloped line is a typical thermal conductivity response of a compensator element). Methane did burn in the well filled with the Atomergic alumina doped with Pd as palladium atoms on alumina near the hot compensator element became catalytically active. This example illustrates that, in addition to insulation and poison tolerance, a catalytic functionality can be built into an insulating material. The catalytic powder insulating material was prepared by doping the alumina with a 10% TAPN solution (0.8 mL solution/1.0 g alumina) and drying it at 500° C.)

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A gas sensor comprising: a housing and a chemically active heated element disposed within the housing, the active element being surrounded by a porous insulating material placed within the housing, the porous insulating material having a bulk density no greater than approximately 0.3 g/cc.

2. The gas sensor of claim 1 wherein the bulk density is no greater than approximately 0.15 g/cc.

3. The gas sensor of claim 1 wherein the bulk density is no greater than approximately 0.1 g/cc.

4. The gas sensor of claim 1 further comprising a compensating element disposed within the housing, the compensating element being surrounded by the porous insulating material.

5. The gas sensor of claim 1 wherein the porous insulating material has an average pore size or diameter of at least approximately 100 Å.

6. The gas sensor of claim 5 wherein the porous insulating material has an average pore size of at least approximately 150 Å.

7. The gas sensor of claim 1 wherein the porous insulating material has a surface area of less than approximately 200 m$^2$/cc.

8. The gas sensor of claim 1 wherein the porous insulating material has a surface area no greater than approximately 100 m$^2$/cc.

9. The gas sensor of claim 1 wherein the porous insulating material has a surface area no greater than approximately 50 m$^2$/cc.

10. The gas sensor of claim 1 wherein the porous insulating material has a surface area no greater than approximately 30 m$^2$/cc.

11. The gas sensor of claim 1 wherein the porous insulating material has a surface area no greater than approximately 20 m$^2$/cc.

12. The gas sensor of claim 1 wherein the porous insulating material has a pore volume of at least approximately 0.05 cc/cc.

13. The gas sensor of claim 8 wherein the porous insulating material has a pore volume of at least approximately 0.10 cc/cc.

14. The gas sensor of claim 1 wherein the porous insulating material comprises a metal oxide or a metalloid oxide.

15. The gas sensor of claim 14 wherein the porous insulating material comprises silica, alumina or zirconia.

16. The gas sensor of claim 1 wherein the active element comprises a platinum wire encased in a refractory bead, a catalyst being supported by the refractory bead.

17. The gas sensor of claim 1 wherein the active element consists essentially of a platinum wire.

18. The gas sensor of claim 1 wherein the porous insulating material is doped with at least one compound suitable to remove a poison.

19. The gas sensor of claim 18 wherein the compound is a copper compound.

20. The gas sensor of claim 19 wherein the compound is a copper sulfate.

21. A gas sensor for the detection of gases comprising, a housing and a chemically active element disposed within the housing, the active element being surrounded by a porous powder material placed within the housing, the porous powder material having an average pore size of at least approximately 100 Å.

22. The gas sensor of claim 21 wherein the porous powder material has an average pore diameter of at least approximately 150 Å.

* * * * *